US006174667B1

(12) United States Patent
Huchzermeier et al.

(10) Patent No.: US 6,174,667 B1
(45) Date of Patent: *Jan. 16, 2001

(54) BOVINE VIRAL DIARRHEA VIRUS SERUM ANTIGEN CAPTURE

(75) Inventors: Roy Huchzermeier, Fayetteville; Edward Joseph Dubovi, Ithaca, both of NY (US)

(73) Assignees: Cornell Research Foundation, Inc.; Syracuse Bioanalytical, Inc., both of Ithaca, NY (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/935,644

(22) Filed: Sep. 23, 1997

(51) Int. Cl.$^7$ .............................. C12Q 1/70; G01N 33/53
(52) U.S. Cl. ................................ 435/5; 435/7.1; 435/7.9; 435/7.92; 435/7.93; 435/7.94
(58) Field of Search .................................. 435/5, 7.1, 7.9, 435/7.92, 7.93, 7.94

(56) References Cited

U.S. PATENT DOCUMENTS

| 5,620,691 | 4/1997 | Wensvoort et al. ............... 424/184.1 |
| 5,648,466 | * 7/1997 | Vandenbergh et al. . |
| 5,705,338 | * 1/1998 | Piran et al. . |

FOREIGN PATENT DOCUMENTS

| 0 236 977 | 9/1987 | (EP) ................................. C07K/7/10 |
| 0 518 756 | 6/1992 | (EP) . |

OTHER PUBLICATIONS

Brock, K. V., etal, Impact of Bovine Viral Diarrhea Virus on Reproductive Performance, 1996, pp. 108–109.
Brownlie, J., Pathogenesis of mucosal disease and molecular aspects of bovine viral diarrhoea virus. 1990, pp. 371–382.
Brownlie, J., Clinical aspects of bovine virus diarrhea/mucosal disease complex in cattle, 1985, Pract. 7:195–202.
Brownlie, J., Variation in Acute Bovine Virus Diarhoea Virus Infections, 1996, pp. 176–181.
Corapi, W.V., etal, Monoclonal antibody analysis of cytopathic and noncytopathic viruses from fatal bovine viral diarrhea virus infections., 1988, pp. 2823–2827.
Corapi, W.V., etal., Characterization of a panel of monoclonal antibodies and their use in the study of the antigenic diversity of bovine viral diarrhea virus, 1990, (9) 1388–1394.
Donis, R. O., et al., Glycoproteins of Bovine Viral Diarrhea–Mucosal Disease Virus in Infected Bovine Cells, 1987, pp. 1607–1616.
Donis, R.O., et al., Characterization of Bovine Viral Diarrhea–Mucosal Disease Virus–specific Proteins in Bovine Cells, 1987, pp. 1597–1605.
Dubovi, E.J., Molecular biology of bovine virus diarrhoea virus, 1990, pp. 105–114.
Evermann, J.F., etal., Clinical Epidemiology of Bovine Viral Diarrhea Virus in the Northwestern United States, 1996, p. 193.
Greiser–Wilke, I., etal., Immunofluorescence Studies of Biotype–Specific Expression of Bovine Viral Diarrhea Virus Epitopes in Infected Cells, 1991, pp. 2015–2020.
Horner, G.W., etal., Comparison of an antigen capture enzyme–linked assay with reverse transcription–polymerase chain reaction and cell culture immunoperoxidase tests for the diagnosis of ruminant pestivirus infections, 1995, pp. 75–84.
Kwang, J., etal., Recombinant Polypeptide from the gp–48 Region of the Bovine Viral Diarrhea Virus BVDV Detects Serum Antibodies in Vaccinated and Infected Cattle, 1992, pp. 281–292.
Meyeres, G., etal., Origin and Diversity of Cytopathogenic Pestiviruses, 1996, pp. 24–34.
Moenning, V., Pestiviruses: a review., 1990, pp. 35–54.
Palfi, V., etal., Studies on the decline of bovine viral diarrhoea virus (BVDV) maternal antibodies and detectability of BVDV in persistently infected calves., 1993, pp. 105–107.
Paton, D., etal., Antigenic Variation Amongst Pestiviruses, 1996, pp. 61–64.
Paton, D.J., etal., Border disease virus: Delineation by monoclonal antibodies, 1994, pp. 241–252.
Radostits, O.M., etal., New concepts in the pathogenesis, diagnosis, and control of diseases caused by the bovine viral diarrhea virus, 1988, pp. 513–528.
Rumenapf, T., etal., Processing of the Envelope Glycoproteins of Pestiviruses, 1993, (6):3288–3294.
Saliki, J.T., Bovine Viral Diarrhea: Clinical Picture in South Central United States, Jun., 1996, pp. 159–166.

(List continued on next page.)

* cited by examiner

Primary Examiner—Anthony C. Caputa
Assistant Examiner—Brenda G. Brumback
(74) Attorney, Agent, or Firm—Nixon Peabody LLP

(57) ABSTRACT

The invention disclosed herein presents an antigen-capture immunoassay that utilizes serum, plasma, milk, urine, saliva, or other bodily fluid samples to identify cattle infected with the Bovine Viral Diarrhea Virus (BVDV). The results of this assay allow an effective, reliable, quick, and cost efficient way to identify, and thereby remove, infected cattle and/or other ruminants from otherwise uninfected herds. The BVD virus causes an acute enteric disease with a variety of clinical manifestations, and is closely related to sheep border disease virus (BDV) and hog cholera virus (HCV). The traditional method of detecting infected animals, including persistently infected (PI) carriers, has been through the use of virus isolation procedures. While this older test methodology can detect infected animals, the virus isolation test can only be performed by highly trained technicians in a highly specialized laboratory facility. The kit disclosed herein uses ELISA methodology, employs the BVDV antigen specific monoclonal antibody 15.c.5, and requires at least 100 μl of sample per assay.

18 Claims, No Drawings

OTHER PUBLICATIONS

Shannon, A.D., etal., An antigen–capture ELISA detects pestivirus antigens in blood and tissues of immunotolerant carrier cattle, 1991, 34:1–12.

Silva–Krott, I.U., etal., Cloning, sequencing, and in vitro expression of glycoprotein gp48 of a noncytopathogenic strain of bovine viral diarrhea virus, 1994, (1–2):1–14.

Stark, R., etal., Genomic Localization of Hog Cholera Virus Glycoproteins, 1990, 174:286–289.

Thiel, H., et al., Pestivirus Proteins and Vaccination, 1996, 112–120.

vanRijn, P.A., etal., Subdivision of Pestiviruses Bases on Genetic and Antigenic Variation of Glycoprotein E2 (gp53), 1996, 206.*

Westway, E.G., etal., Toga Viridae, Intervirology, 1985, 24:125–139.*

Salikie et al., Journal of Clinical Microbiology, 35 (4):803–807, Apr. 1997.

Meyling, A., "Detection of BVD Virus in Viremic Cattle by an Indirect Immunoperoxidase Technique," In M.S. McNutty and J.B. MacFerran (ed.), Recent Advances in Virus Diagnosis, Martinus Nijhoff Publishers, Boston, Massachussets, pp. 37–46 (1984).*

Bezek, "Induction of Thrombocytopenia With Bovine Viral Diarrhea Virus in Acutely and Persistently Infected Cattle," Ph.D. Thesis, Catalogued at Cornell University (1992).*

Entrican et al., Veterinary Microbiology, 43:65–74, 1995.*

Gottschalk et al., Journal of Veterinary Medicine, 39:247*472, 1992.*

Mignon et al., Journal of Virological Methods, 35:177–188, 1991.*

Shannon et al., Journal of Virological Methods, 34:1–12, 1994.*

Haines et al., Veterinary Pathology, 29:27–32, 1992.

Alkan et al., Journal of Immunoassay, 15/3:217–238, 1994.

Waris et al., Journal of Clinical Microbiology, 26/12:2581–2585, 1988.

BOVINE VIRAL DIARRHEA VIRUS SERUM ANTIGEN CAPTURE

FIELD OF THE INVENTION

The invention pertains to the field of immunoassay tests for viral infection. More particularly, the invention pertains to the development of an antigen-capture immunoassay which can use serum, plasma, milk, mucosal fluid, or urine samples to identify animals infected with the bovine viral diarrhea virus.

BACKGROUND OF THE INVENTION

Bovine viral diarrhea virus (BVDV) currently represents a major threat to the cattle industry. First described over fifty years ago, this pathogen has been found to be both highly virulent and easily spread. Considered a primary pathogen of the bovine enteric, respiratory, reproductive, and immune systems, BVDV continues to cause significant economic losses to the cattle industry worldwide. Recent outbreaks have occurred in Canada, the U.S., and throughout the world. To help combat these problems, a simpler, more cost effective method of BVDV detection, capable of yielding results in a timely fashion, is needed to better control the spread of the BVDV virus within the cattle population. Such a diagnostic tool is particularly important in light of the ineffectiveness of currently available BVDV vaccines.

Classified as a member of the genus Pestivirus and Flaviviridae family, BVDV is closely related to sheep border disease virus (BDV), and hog cholera virus (HCV), both of which are serologically related pestiviruses. Entire or partial genomic sequencing of pestivirus isolates has allowed the determination that a high degree of sequence conservation is present among the pestiviruses. More recently, antigenic variants of BVDV have been identified, and BVDV strains have been divided into two distinct genotypes, type 1 and type 2, which have been further subdivided, based upon cytopathogenicity. Molecular cloning, and Polymerase Chain Reaction (PCR) technology have determined that the general structure of BVDV consists of a capsid protein and three envelope glycoproteins. The genome of BVDV is a 12.3 kb RNA consisting of a single open reading frame (ORF). The BVD virus is itself a small, enveloped RNA virus with positive strand polarity. This positive strand aspect of the viral genome allows the RNA to be infectious, even in the absence of virion proteins.

The BVDV is spread through the herd in a fecal-oral manner, attacking the enteric, respiratory, reproductive, and immune systems. The viral load needed to provoke symptomatic infection is correlated with the type and strain of BVD virus. In addition, BVDV has the ability to infect fetuses by crossing the placenta, often resulting in a spontaneous abortion of the fetus, and a resultant decreased fertility among infected animals. Strategies for control of BVDV range from stricter management practices, in an effort to simply reduce economic loss, to elaborate testing procedures to identify infected animals that, while effective, would entail an unacceptable level of cost. Failure of field vaccinations for BVDV have increased the need for a test protocol that will help identify and eliminate infected animals in a cost-effective way.

It should also be noted that BVDV, like other infectious disease agents, is associated with a wide variety of clinical manifestations, creating a very difficult diagnostic challenge. Common manifestations of BVDV infection can include: abortion storms, infertility, irregular heat cycles, early embryonic deaths, fetal mummification, immuno-suppression, dysentery, thrombocytopenia, and cerebral hypoplasia. Moreover, serological studies have shown that a high percentage of cattle infected with BVDV, including those considered to be persistently infected (PI), remain clinically asymptomatic. Such conditions make it imperative that a reliable, inexpensive, and easy to use test be developed to assist in the detection of BVDV-infected animals in cattle herds.

The BVD virus is typically maintained in a herd due to the presence of immuno-tolerant persistently infected carrier animals. These PI cattle are exposed to the virus in utero, but can remain clinically asymptomatic throughout the course of their lives, continually shedding fecal matter, and bodily fluids, with a high concentration of virus, and thereby posing the threat of infection for other animals as long as they remain in the herd. The virus may be present in more than half of the cattle in a herd before signs of an outbreak exhibit themselves. Symptoms of the disease are usually preceded by leukopenia, and testing efforts to date have focused on identifying this effect.

Prior outbreaks have resulted in crippling economic losses to the livestock industry; for example, in Ontario in 1993, BVDV cases increased 23% in less than one year. It should also be noted that although the historical assignment of BVDV as a pestivirus was through the species it was first found to be associated with (e.g. cattle), it is now known that pestiviruses can cross species barriers. This indicates that in areas in which wild, free-ranging ruminants (moose, buffalo, etc.) are exposed to infected cattle herds, these animals are also susceptible to infection from BVDV, or can alternatively act as a reservoir of virus capable of infecting a previously "clean" herd.

Over one hundred and fifty vaccines for BVDV have been marketed to cattle farmers over the past thirty years. These vaccines have consisted of modified live BVD virus or inactivated attenuated virus and virus particles. Recent BVDV outbreaks have occurred, however, despite the availability and use of these vaccines. Current approaches to vaccination involve repeated yearly inoculation with vaccine for cattle, and additional steps are generally taken in an attempt to assure that no calves are born as PI carriers. However, for effective control of the BVD virus to be possible, it is essential to identify the PI animals and remove them from the herd. Several different test methods have been developed for the detection of BVDV, and/or the detection of BVDV infected animals. These test methods include: reverse transcription-polymerase chain reaction, enzyme-linked immunoassay (ELISA), and standard virus isolation techniques.

Both PCR and virus isolation techniques, owing to their inherent sensitivity are each capable of detecting very low levels of BVDV virus. However, these methods are also time-consuming, relatively complex, and expensive. ELISA technology, although somewhat less sensitive, is better suited as a broad-based diagnostic tool. However, until this disclosure, antigen-disclosure ELISA tests for BVDV have continued to rely on the use of white blood cell extracts from the animal to be tested. White blood cell extracts have been necessary because BVDV proteins accumulate to relatively high concentrations within the white blood cells of infected animals, and the previous ELISA methods lacked the sensitivity to detect their target BVDV proteins in blood serum. (Homer et al., 1995). The preparation of white cell extracts is itself time consuming and relatively expensive, making any ELISA test reliant upon this extraction costly in and of itself. Thus, with regard to the methods supplied by the prior art as a whole, not only are they time-consuming, as already suggested, but they often require sophisticated laboratory facilities and highly trained technicians to complete. For this reason they are economically prohibitive to use in the broad fashion that is required for today's cattle industry.

Radioimmunoprecipitation (RIP) studies of BVDV infected cattle, have indicated a strong immune response to several BVDV glycoproteins (Donis and Dubovi 1987), including gp53$^{E2}$, gp48, and gp25. The strength of the response to these, and other, glycoproteins, has made them targets for further study of BVDV gene expression and cytopathicity. In the course of this study, Corapi et al., (1988) generated the 15.c.5 mAb. It was found that the target for this mAb was an epitope of the BVDV gp48 (alternatively known as "EO" or $E^{ms}$ in the literature). Thereafter it was suggested by Kwang et al., (1992) that this mAb could be important in the development of a competitive ELISA detection assay for an antibody to BVDV, possibly using cattle sera as the sample. It must be pointed out though that Kwang did not suggest the potential use of this antibody (e.g. mAb 15.c.5) in an antigen-capture ELISA.

The generation of the 15.c.5 monoclonal antibody (Corapi, et al., 1988) and subsequent discovery that relatively high levels of a particular BVDV protein (gp48) could be detected in the serum of BVDV-infected animals by utilizing 15.c.5 as a capture antibody (Huchzermeier, et al., 1996), led to the invention herein described. The mAb 15.c.5 is currently available through the Diagnostic Laboratory at the College of Veterinary Medicine, Cornell University, Ithaca N.Y.

SUMMARY OF THE INVENTION

An ELISA test has been developed which utilizes a monoclonal antibody (mAb), specific for BVDV viral proteins or protein fragments, to recognize their presence in bovine serum, plasma, milk, urine, or mucosal fluid. The important aspect of this ELISA test is that this ELISA provides for the detection of the target viral proteins in serum, milk, plasma or other bodily fluid. Typically white blood cells must be collected and extracted, requiring a time consuming and labor intensive sample preparation procedure. Through the use of the mAb 15.c.5 which allows the development of an assay for BVDV from sera, plasma, milk, urine or mucosal fluid, Applicants found that they were able to construct a distinctly improved immunoassay test kit. The immunoassay provided thereby is accurate, has a shorter turn around time for a given test sample, and is an economically much more feasible option for those in the cattle industry. The target epitope of this mAb is located on gp48, also known as "$E^{ms}$" and "EO".

Applicants have optimized their ELISA test such that it has enhanced reliability, and reveals excellent agreement when compared with the conventional, and most sensitive, method of BVDV detection—viral isolation. Applicants have developed their bovine ELISA into an easy to use, reliable, quick, and cost effective kit that will aid veterinarians in their efforts to identify BVDV infected animals, especially those PI animals, and remove them from a given herd. This in turn protects the cattle industry from significant economic loss due to BVDV. Since BVDV can affect other ruminants this assay can be used on wild animal populations (e.g. deer, moose, elk) to determine if they are BVDV positive. This use could aid in the management of wild animal populations and assist in the removal of reservoirs of BVDV virus outside the domestic cattle population.

DESCRIPTION OF THE PREFERRED EMBODIMENT

Bovine Virus Diarrhea (BVDV)-Antigen Test

As already stated, BVDV maintains itself in the bovine population through persistently infected (PI) animals. This type of animal results from fetal infection with the BVD virus. If the fetus survives to term, the resulting calf will be incapable of mounting an immune response against the virus and will be persistently infected with the virus for the rest of its life. A PI animal may live for years; during this time it will excrete a large quantity of virus into the environment and remain potentially infective to other animals.

Assay Architectures

The BVDV serum immunoassay can be either a sandwich type immunoassay, employing the GP-48 specific antibody (as capture or detector antibody) and another anti-BVDV antibody (as a detector or capture antibody to complement the GP-48 specific monoclonal), or a competitive type immunoassay, employing the GP-48 specific monoclonal antibody with a labeled GP-48 antigen or GP-48 antigen attached to a solid phase.

A variety of configurations and formats are possible for each type of immunoassay. The capture antibody, for example, can be attached to a variety of different solid phases to enable the washing away of unreacted assay reagents during the course of the assay. These include: microwells, coated test tubes, coated magnetic particles, wands or sticks, and membranes (nitrocellulose and others).

The capture antibody, also referred to as primary antibody, can be attached by passive adsorption, covalent coupling, or by using a solid phase pre-coated with a secondary binder such as protein A, protein G, a secondary antibody specific for the primary antibody, avidin, or an antibody specific for a particular ligand (i.e.: biotin, dinitrophenol, fluorescein, and others)—(In the case of avidin or any of the ligand specific antibodies, it is necessary to covalently attach the ligand to the capture antibody).

For a competitive type assay, the GP-48 antigen can be attached to a solid phase by passive adsorption, covalent coupling, or by using a solid phase pre-coated with a secondary binder such as avidin or an antibody specific for a particular ligand such as dinitrophenol, fluorescein and others. (In the case of avidin or any of the ligand specific antibodies, it is necessary to covalently attach the ligand to the GP-48 antigen.)

A variety of labels can be employed in sandwich or competitive type immunoassays. The possibilities include: an enzyme such as peroxidase or alkaline phosphatase, a fluorophore such as fluorescein, a chemiluminescent probe such as an acridinium ester, a time-resolved fluorescent probe such as a europium chelate, a radioactive species, or particles such as colloidal gold, plain latex, or dyed latex.

The GP-48 specific monoclonal antibody or the anti-BVDV antibody can be either directly labeled by covalent coupling or a labeled secondary antibody that is specific for the corresponding primary antibody and can be used without the need to chemically modify the primary antibody. A labeled secondary binder such as avidin or a labeled antibody specific for a particular ligand (i.e.: dinitrophenal, fluorescein, and others) can also be employed. In the case of avidin or any of the ligand specific antibodies, it is necessary to covalently attach the corresponding ligand to the primary antibody.

For a competitive type assay, the GP-48 antigen can be labeled directly by covalent coupling or a labeled secondary binder such as avidin or a labeled antibody specific for a particular ligand (i.e.: dinitrophenol, fluorescein, and others) can be employed. In the case of avidin or any of the ligand specific antibodies, it is necessary to covalently attach the corresponding ligand to the GP-48 antigen.

The Test Kit

Historically, persistently infected (PI) animals have been identified by testing blood samples from these animals using a virus isolation procedure. While this test methodology can detect infected animals, the virus isolation test can only be performed by highly trained technicians in a highly specialized laboratory facility. The BVDV antigen test for serum, disclosed herein by the Applicants, in contrast, represents a simpler, faster, and less expensive means of detecting BVDV antigen in serum, plasma, milk, urine, or mucosal fluid samples from infected animals. This kit claimed herein is based on the ELISA methodology, and it employs a BVDV antigen specific monoclonal antibody as the capture antibody, with a goat polyclonal anti-BVDV antibody as the detector, and a Horseradish Peroxidase—anti-goat antibody as the conjugate. The test results may be determined through the use of a microplate spectrophotometer wherein an optical density is read at 450 nanometers.

To create the ELISA technology disclosed herein, the concentration of detector antibody, the particular anti-goat conjugate and its concentration, the formulation of the reagent diluent buffer, the formulation of the NSB (non-specific binding) reagent; and the type of microwell were all optimized to yield the lowest background and highest signal-to-noise ratio. Furthermore, the reagent configuration (i.e. 10x concentrates of detector reagent, enzyme conjugate reagent and NSB reagent, with a separate reagent diluent buffer was designed to maximize kit stability and shelf life.

In addition to this work, there were two breakthroughs that made this serum assay possible. First, it was found that a small amount of bovine gamma globulin was a key additive in the reagent diluent buffer (this reagent diluent buffer is used to prepare working solutions of detector antibody and enzyme conjugate); this additive significantly reduced the background signal.

The second breakthrough involved well coating. It is advantageous to utilize a purified monoclonal antibody rather than a crude ascites preparation for well coating to insure consistency between batches of coated microplates. When purified 15.c.5 was coated onto wells, however, the background signal was found to be unacceptably high. It was discovered that this high background problem could be alleviated by the addition of bovine albumin to the purified 15.c.5 prior to well coating.

The ELISA procedure is carried out at room temperature, and takes approximately 4 hours to complete, though it does not require highly specialized laboratory facilities.

Sample Requirements

The volume of sample (serum, plasma, milk, urine, or mucosal fluid) required for purposes of this assay procedure is at least 100 $\mu$l per well. Only samples from pre-colostral newborn calves or calves older than 3 months of age are suitable for testing in this ELISA kit. Maternal anti-BVDV antibodies, which can be passed to newborn calves in the first 24 hours of colostrum intake, can interfere with this ELISA to produce false negative results in PI calves. Since the level of maternal antibody decreases as the calf ages, this interference can be prevented by specifying age requirements for animals being tested by this ELISA (Palfi et al., 1993).

Components of the BVDV Antigen Test Kit

With regard to the components of the test kit, each kit will contain one negative control and one positive control. These controls will be included within each run to insure that each run is valid and to be used in the data reduction calculation (to "normalize" the sample results). These controls, as well as all the other reagents used in the assay presented in this application are preserved with the addition of thimerosal.

To minimize the necessary container volumes and maximize kit stability, the detector reagent, enzyme conjugate reagent, non-specific binding inhibiting reagent (e.g. the "NSB" reagent) and the ELISA wash buffer are supplied as 10X concentrates. The Reagent Diluent Buffer, the negative control, the positive control, TMB substrate reagent, and a solution that will stop the reaction (e.g. "Stop Solution") are supplied in the kit in a ready-truse form with no need for dilution. The samples are run in one of two 96-well plates provided in the kit.

Other compounds or resources needed to perform the BVDV Antigen Test Kit ELISA include among other things: de-ionized water, a microplate reader capable of making an optical density (OD) reading at 450 nm, serological pipets, and precision pipettors. Directions for the preparation of reagents is included within the literature included with the kit, and broadly refers to the proper procedures and use of the reagents provided in the kit.

Reagent Composition

It should be noted that working solutions of the detector reagent and enzyme conjugate reagents should be made within approximately 1 hour of anticipated use and then stored at 4° C.

ELISA Wash Buffer—10X concentrate

The compounds comprising the ELISA Wash Buffer are: 1 M Tris; HCl (6.25Normal) for pH adjustment; 0.01% Thimerosal; and 5% Tween 20.

Detector Reagent—10X concentrate

The compounds comprising the Detector Reagent are: 25% Ethylene Glycol, 0.01% Thimerosal, approximately 5% goat anti-BVD antibody, and 0.06% yellow food coloring in PBS (pH 7.4).

NSB Reagent—10X concentrate

The compounds comprising the NSB reagent are: 25% Ethylene Glycol, 0.01% Thimerosal, 0.2% Mouse IgG, 0.06% red food coloring in PBS (pH 7.4).

Reagent Diluent Buffer

The compounds comprising the Reagent Diluent Buffer are: 2.5% Bovine Serum Albumin, 0.01% Thimerosal, and 1.0% bovine gamma globulin in PBS (pH 7.4).

TMB Substrate Reagent

A commercially available TMB substrate is used. Suppliers of this substrate include: Boehringer Mannheim Corp., Pierce Chemical Co., and Kirkegaard & Perry Laboratories.

Stop Solution

The stop solution consists of 1% hydrochloric acid (HCl). It is typically purchased as a ready to use reagent from Kirkegaard and Perry Laboratories.

Anti-BVDV Antibody-Coated Wells

Each 96-well tray is coated overnight with 0.1 ml per well of a solution containing purified 15.c.5 at 5 $\mu$g/ml and bovine serum albumin at 10 $\mu$g/ml in carbonate buffer (pH9.6). Following the coating, each tray is washed three times with ELISA wash buffer and allowed to dry overnight at 4° C. A foil pouch is used to encase each tray after drying, and a desiccant is included inside each pouch to remove moisture.

Enzyme Conjugate Reagent—10X concentrate

The compounds comprising the Enzyme conjugate reagent are: 25% Ethylene Glycol, 0.01% Thimerosal, anti-goat antibody conjugated to detection mechanism, typically horseradish peroxidase (dilution approximately 1 to 700), 0.1% rabbit albumin, and 0.02% rabbit gamma globulin in PBS (pH7.4).

Negative Control

The compounds comprising the negative control for the assay kit are: 1% Igepal, and 0.01% Thimerosal in PBS (pH 7.4).

Positive Control

The compounds comprising the positive control for the assay kit are: 1% Igepal, 0.01% Thimerosal, 1% Bovine Serum Albumin, BVD culture (dilution approximately 1:20)and 50 µM phenyl methyl sulfonyl fluoride in PBS (pH7.4).

ELISA Protocol

To run the ELISA the user should employ the needed number of microwells from one or more of the provided 96-well plates. The microwells themselves can be removed from the plates provided, any excess wells should be saved for future assays. The wells are first pre-wetted by pipetting 0.2 ml of ELISA Wash Buffer into each well; this buffer should then be removed or poured off the wells prior to the addition of sample. As with each of the wash steps, it is important that all ELISA Wash Buffer added to the wells is removed, while also insuring that the wells do not dry out between steps. Thereafter pipette 100 µl of sample or control into each well.

After addition of the sample or control cover the wells with the self-adhesive transparent film cut to the appropriate size, and incubate the wells at room temperature for 1 to 1.5 hours. The working Detector Reagent should then be prepared by mixing 1 part of the Detector Reagent—10X concentrate, 1 part of NSB Reagent 10X concentrate, and 8 parts of Reagent Diluent Buffer. This working agent should be prepared within approximately 1 hour of anticipated use.

After the incubation period, remove liquid from the wells as described above and wash them by adding 0.2 ml of ELISA Wash Buffer to each well and then removing or pouring off the ELISA Wash Buffer. This wash process should be repeated two more times to yield a total of three washes. After this step 0.1 ml of working Detector Reagent should be pipetted into each sample and control microwell. Cover the wells with the adhesive film and incubate at room temp. for 1 to 1.5 hours. During this time the working Enzyme Conjugate Reagent should be prepared, by mixing 1 part of enzyme conjugate reagent—10X concentrate, 1 part of NSB Reagent—10X concentrate, and 8 parts of Reagent Diluent buffer. This working reagent should be prepared within approximately 1 hour of anticipated use. After the incubation period, remove liquid from the wells as described above, and wash the wells a total of three times as described above. Thereafter pippette 0.1 ml of working Enzyme Conjugate Reagent into each microwell. When this is accomplished cover the wells with adhesive film and incubate at room temperature for 1 to 1.5 hours. While this incubation is ongoing retrieve the TMB Substrate Reagent and Stop Solution and allow them to equilibrate at room temperature or remain at room temperature.

After the incubation period remove the liquid from the wells and wash the wells a total of three times, as described above. Pipette 0.1 ml of TMB substrate reagent into each microwell. To avoid contamination of the TMB Substrate, it is recommended that the quantity of TMB to be used should be poured out of its bottle into a separate container for pipetting and that any left over TMB be discarded rather than returned to its original container. After the TMB substrate reagent has been put into the wells cover them and incubate at Room Temperature (RT) in the dark for 10 to 12 minutes. After this incubation period pipette 0.1 ml of Stop Solution into each microwell, and again incubate at RT in the dark for 5 to 10 minutes. Once this final incubation is completed the BVDV status of the samples is ready to be read at 450 nm, against an air or water blank on a microplate reader, or other suitable spectrophotometer.

With regard to the above protocol, it should be noted that to insure the accuracy and quality of results reached, both positive and negative controls should be included in every ELISA run. The BVDV Antigen Test Kit itself should be stored at 2–8° C. in order to maintain its shelf life and effectiveness for as long as possible.

ELISA Data Reduction

The data is reduced by first calculating the average raw OD (optical density) for each control and sample assayed. The average OD value obtained for the Negative Control is then subtracted from each of the other average raw OD values to obtain blank-corrected OD values for the corresponding positive control and samples. This step eliminates the background noise (due to non-specific binding of enzyme conjugate) from the specific signal. A "normalized" OD is then calculated for each sample by dividing the blank-corrected OD of that sample by the "blank-corrected" OD of the Positive Control. Normalizing the results in this manner greatly diminishes the run-to-run variation. The normalized OD values thus gained are compared with the following guidelines to determine the BVDV status of the animal, see Table 1, below.

TABLE 1

| Optical Density Chart for the Determination of BVDV Status | |
| --- | --- |
| "Normalized" OD Values | BVDV Status |
| Less than 0.20 | BVDV NEGATIVE |
| 0.20 to 0.39 | "Gray Zone" |
| Greater than 0.39 | BVDV POSITIVE |

With regard to the above comparison, if a "Normalized" OD is obtained that is within the "gray zone", the sample should be re-assayed using the standard working reagents as previously used and also assayed without detector antibody in the working detector antibody reagent.

The raw OD obtained without detector should be subtracted from the raw OD obtained with detector; this difference should then be divided by the blanked OD of the positive kit control (the OD of the negative kit control should be used to blank the positive kit control as usual). A new normalized value less than 0.2 should be considered BVDV negative, a new normalized OD value of 0.2 or greater should be considered BVDV-positive.

Quality Control

In order to maintain consistently reliable data, raw OD values (e.g., unblanked) obtained for the kit—with regard to the positive and negative controls—should fall within the ranges seen in Table 2.

TABLE 2

Unblanked Optical Density Standards for Reliability

Raw OD Values

| | |
|---|---|
| Negative Control | <0.5 |
| Positive Control | >0.8 |

TABLE 3

ELISA results on bovine serum samples using the purified 15.c.5 preparation as capture antibody on the microwells (A total of 129 animals were tested; Viral Isolation Results were used as a correct reference determination.)

| | BVDV-negative by virus isolation | BVDV-positive by virus isolation | Confirmed PI animals |
|---|---|---|---|
| The number of samples tested in each category BVDV Ag Test Kit results for each category of samples | 104 | 25 | 7 |
| Number of test kit negatives | 104 | 0 | 0 |
| Number of test kit positives | 0 | 25 | 7 |

Expected Results

To determine the accuracy of the ELISA methodology a total of 129 domestic cattle were tested in a method comparison study. This group included 104 known BVDV-negative samples and 25 known BVDV-positive samples, as defined by a reference Virus Isolation procedure.

Using the positive, negative, and gray-zone ELISA cutoffs, described previously in the Data Reduction section, all BVDV-negative animals yielded negative ELISA results, as seen in Table 3. A mean Normalized OD value of 0.06 was obtained with a standard deviation of 0.03 for these BVDV-negative samples. Normalized OD values for these samples ranged from 0.02 to 0.14, with all samples yielding Normalized OD values below 0.20.

Twenty-five of the 25 BVDV-positive samples (as defined by Reference Virus Isolation) were found to be positive in the ELISA. Normalized OD values for these 25 positive samples ranged from 0.56 to 1.16, with a mean of 0.85 and standard deviation of 0.15.

Since an acute BVDV infection can result in the production of viral antigens over a short period of time, a BVDV-Positive result in the ELISA may not always be indicative of a persistently infected animal. A definitive diagnosis that a particular animal is persistently infected should only be made after a second sample is taken from the subject animal at least 3 weeks after the initial sample and that second sample is also found to be BVDV-positive.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of detecting whether a target animal is Bovine Viral Diarrhea Virus positive or negative comprising:

a) providing at least one sample taken from said target animal, wherein said sample is selected from the group consisting of blood serum, mucosal fluids, milk, blood plasma, and urine;

b) providing an assay system which comprises:
      1) a capture antibody that is a Bovine Viral Diarrhea Virus epitope specific antibody, said capture antibody being immobilized on a solid support and capable of recognizing and binding a gp48 Bovine Viral Diarrhea Virus protein or protein fragment thereof which retains antigenic specificity;
      2) a detector antibody that is an anti-Bovine Viral Diarrhea Virus antibody, capable of recognizing and binding said gp48 Bovine Viral Diarrhea Virus protein or protein fragment thereof which retains antigenic specificity;
      3) a signal generator for indicating the presence of said detector antibody operatively associated with Bovine Viral Diarrhea Virus antigen;

c) analyzing the sample with said assay system to generate a change in signal if Bovine Viral Diarrhea Virus antigen is present in the sample; and d) comparing the signal to one or more reference levels to indicate whether the target animal is Bovine Viral Diarrhea Virus positive or negative.

2. The method of claim 1 wherein said assay system includes a quantity of said capture antibody sufficient to optimize the detection of said gp48 Bovine Viral Diarrhea Virus protein or said protein fragment from said at least one sample taken from said target animal.

3. The method of claim 1 where said Bovine Viral Diarrhea Virus epitope specific antibody is the monoclonal antibody designated as 15.c.5.

4. The method of claim 1 where said capture antibody is a polyclonal antibody.

5. The method of claim 1 where said capture antibody is a monoclonal antibody.

6. The method of claim 1 where the signal generator has a marker directly conjugated to said detector antibody.

7. The method of claim 1 where said anti-Bovine Viral Diarrhea Virus detector antibody is a polyclonal antibody.

8. The method of claim 1 where said anti-Bovine Viral Diarrhea Virus detector antibody is a monoclonal antibody.

9. The method of claim 1 where said signal generator is selected from the group consisting of:
   a) peroxidase;
   b) alkaline phosphatase;
   c) a fluorophore;
   d) a chemiluminescent probe;
   e) a time-resolved probe;
   f) a radioactive species;
   g) particles of colloidal gold;
   h) plain latex;
   i) horseradish peroxidase; and
   j) dyed latex.

10. The method of claim 9, wherein the fluorophore is fluorescein.

11. The method of claim 9, wherein the chemiluminescent probe is an acridinium ester.

12. The method of claim 9, wherein the time-resolved fluorescent probe is a europium chelate.

13. A method of detecting Bovine Viral Diarrhea Virus infection in a bovine comprising:

providing a sample of blood serum, mucosal fluid, milk, blood plasma, or urine from the bovine;

contacting the sample with a gp48 Bovine Viral Diarrhea Virus protein-specific reagent; and analyzing whether the gp48 Bovine Viral Diarrhea Virus protein-specific reagent binds to a gp48 Bovine Viral Diarrhea Virus protein or protein fragment thereof, which retains antigenic specificity, from the sample.

14. A method according to claim 13, wherein said analyzing is carried out with a polyclonal antibody.

15. A method according to claim 13, wherein said analyzing is carried out with a monoclonal antibody.

16. A method according to claim 15, wherein the monoclonal antibody is 15.c.5.

17. A method according to claim 13, wherein said analyzing is carried out with a sandwich immunoassay.

18. A method according to claim 13, wherein said analyzing is carried out in a competitive immunoassay.

* * * * *